United States Patent [19]

Lui et al.

[11] Patent Number: 5,621,111
[45] Date of Patent: Apr. 15, 1997

[54] PROCESS FOR THE PREPARATION OF SIDE CHAIN-FLUORINATED ALKYLOXAZOLES, AND NEW SIDE CHAIN-FLUORINATED ALKYLOXAZOLES

[75] Inventors: Norbert Lui, Cologne; Albrecht Marhold, Leverkusen, both of Germany

[73] Assignee: Bayer Aktiengesellschaft, Leverkusen, Germany

[21] Appl. No.: 544,245

[22] Filed: Oct. 17, 1995

[30] Foreign Application Priority Data

Oct. 24, 1994 [DE] Germany ................. 44 37 932.3

[51] Int. Cl.$^6$ .................. C07D 263/04; C07D 263/14
[52] U.S. Cl. ................ 548/215; 548/237; 548/239
[58] Field of Search ..................... 548/237, 239, 548/215

[56] References Cited

U.S. PATENT DOCUMENTS 4,235,892 11/1980 Nagabhushan .................. 564/86 X
4,876,352 10/1989 Schumacher et al. ............. 548/232

FOREIGN PATENT DOCUMENTS 9002739 3/1990 WIPO .
9414764 7/1994 WIPO .

OTHER PUBLICATIONS

A. Takaoka, et al., Bull. Chem. Soc. Japan, vol. 52, No. 11, pp. 3377–3380, (1979).

Primary Examiner—Jacqueline Haley
Attorney, Agent, or Firm—Sprung, Horn Kramer & Woods

[57] ABSTRACT

A process for the preparation of side chain-fluorinated alkyloxazoles, wherein hydroxyalkyloxazoles are reacted with an α,α-difluoroalkylamine at pressures of under 2 bar, in the presence of an inert solvent boiling at above 100° C. (at normal pressure), and new fluorinated alkyloxazoles.

8 Claims, No Drawings

PROCESS FOR THE PREPARATION OF SIDE CHAIN-FLUORINATED ALKYLOXAZOLES, AND NEW SIDE CHAIN-FLUORINATED ALKYLOXAZOLES

The present invention relates to a particularly advantageous process for the preparation of fluorinated alkyloxazoles, which are important as intermediates for the preparation of antibiotics against gram-positive, gram-negative and against thiamphenicol-resistant microorganisms (see e.g. U.S. Pat. No. 4,235,892), and new side chain-fluorinated alkyloxazoles, which can be used for the same purpose.

U.S. Pat. No. 4,876,352 discloses that certain hydroxyalkyloxazolines can be reacted with α,α-difluoroalkylamines under pressure to give the corresponding fluoro derivatives. Suitable pressures here are e.g. those from 60 to 100 psi (about 4.2 to 7 bar); the solvent used is in particular methylene chloride (see claims 2 and 5 and the examples there). A disadvantage is working under pressure, which requires particular technical outlay, and the preferred use of methylene chloride, which for ecological reasons requires particular industrial safety measures.

There has now been found a process for the preparation of side chain-fluorinated alkyloxazoles of the formula (I)

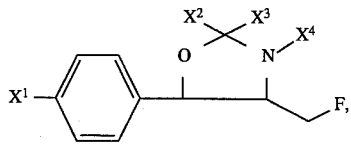

in which
$X^1$ represents hydrogen, nitro, $C_1$-$C_6$-alkylthio, $C_1$-$C_6$-alkylsulpho, $C_1$-$C_6$-alkylthio substituted by fluorine, $C_1$-$C_6$-alkylsulphonyl substituted by fluorine or $C_1$-$C_6$-alkoxy substituted by fluorine, $X^2$ represents $C_1$-$C_6$-alkyl, $C_1$-$C_6$-halogenoalkyl, $C_5$-$C_6$-cycloalkyl, $C_2$-$C_6$-alkenyl, $C_2$-$C_6$-alkinyl, $C_1$-$C_6$-alkoxy, $C_7$-$C_{14}$-aralkyl, $C_8$-$C_{15}$-aralkenyl, $C_6$-$C_{12}$-aryl or a heterocyclic radical having 4 to 11 C atoms and 1 to 3 oxygen, sulphur and/or nitrogen atoms, $X^3$ represents hydrogen or one of the radicals indicated in the case of $X^2$ or $X^2$ and $X^3$ together represent an oxygen atom and $X^4$ represents hydrogen or $X^3$ and $X^4$ together represent a covalent bond, in which the appropriate hydroxyalkyloxazole of the formula (II)

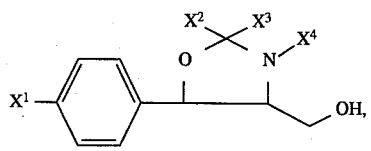

in which the radicals $X^1$ to $X^4$ have the meaning indicated in formula (I), is reacted with an α,α-difluoroalkylamine of the formula (III)

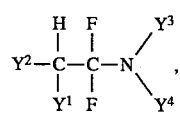

in which
$Y^1$ represents fluorine or chlorine, $Y^2$ represents fluorine, chlorine or trifluoromethyl and $Y^3$ and $Y^4$ independently of one another represent $C_1$-$C_6$-alkyl or $Y^3$ and $Y^4$ together represent a saturated or unsaturated hydrocarbon chain having 4 to 5 C atoms, which is characterized in that the reaction is carried out at pressures of under 2 bar and in the presence of an inert solvent boiling at above 100° C. (at normal pressure).

The compounds of the formula (II) where $X^1$=hydrogen, nitro, $C_1$-$C_6$-alkylthio or $C_1$-$C_6$-alkylsulpho can be obtained, for example, according to EP-A1 130 633 or J. Chem. Soc. 1949, 589–594 or analogously thereto and the compounds of the formula (III), for example, according to U.S. Pat. No. 3,153,644 or Bull. Chem. Soc. Japan 1979, 3377 to 3380 or analogously thereto. The other compounds of the formula (II) can be prepared analogously to U.S. Pat. No. 2,816,915 and EP-A1 130 633 or J. Chem. Soc. 1949, 589–594.

In the formulae (I) and (II),
$X^1$ preferably represents $C_1$-$C_3$-alkylsulphonyl, in particular methylsulphonyl, $X^2$ preferably represents phenyl or naphthyl, in particular phenyl and $X^3$ and $X^4$ preferably together represent a covalent bond.

Preferred compounds of the formula (III) are:
N-(2-chloro-1,1,2-trifluoroethyl)diethylamine,
N-(1,1,2,3,3,3-hexafluoropropyl)diethylamine and
N-(1,1,2,3,3,3-hexafluoropropyl)dibutylamine.

Relative to 1 mol of a compound of the formula (II), 0.8 to 5 equivalents, for example, of a compound of the formula (III) can be employed. This amount is preferably 1.3 to 3 equivalents.

The process according to the invention is carried out at pressures of below 2 bar. Preferred pressures are those in the range of 0.1 to 1.5 bar. The process is particularly preferably carried out under normal pressure.

Suitable inert solvents boiling at above 100° C. at normal pressure are, for example, tetramethylene sulphone, chlorobenzene, dichlorobenzenes and trichlorobenzenes.

Suitable reaction temperatures are e.g. those in the range 70° to 150° C. Preferred temperatures are those in the range 90° to 120° C.

If desired, the reaction according to the invention can be carried out under an inert gas atmosphere, e.g. nitrogen.

The reaction mixture present after the reaction according to the invention can be worked up, for example, by diluting it with water, separating it into an organic and an aqueous phase, extracting the aqueous phase with a water-immiscible organic solvent, for example a water-immiscible ether, washing the organic phase with water, combining the organic phase and the organic extract from the aqueous phase and, optionally after drying, removing the solvent, e.g. by distillation in vacuo.

The process according to the invention has the advantage that it avoids working under pressure which is absolutely necessary according to U.S. Pat. No. 4,876,352 and in spite of this yields the compounds of the formula (I) in good yields.

The present invention furthermore relates to new side chain-fluorinated alkyloxazoles of the formula (I), in which $X^1$ represents fluorine-substituted $C_1$-$C_6$-alkylthio, fluorine-substituted $C_1$-$C_6$-alkylsulphonyl or fluorine-substituted $C_1$-$C_6$-alkoxy and the other symbols have the meaning indicated above. The $C_1$-$C_6$-alkylthio, $C_1$-$C_6$-alkylsulphonyl and $C_1$-$C_6$-alkoxy groups can in each case be monofluorinated or polyfluorinated or perfluorinated.

Preferred new fluorinated alkyloxazoles of the formula (I) are those in which $X^1$ represents methyl- or ethylthio substituted by 1 to 3 F atoms, methyl- or ethylsulphonyl substituted by 1 to 3 F atoms or methoxy or ethoxy substituted by 1 to 3 F atoms and the other symbols have the meaning indicated as preferred above.

EXAMPLES

Example 1

20 g of D-threo-(–)-2-phenyl-4-(4-(methylsulphonyl)phenyl)-2-oxazole-5-methanol and 17.5 g of N-(1,1,2,3,3,3-hexafluoropropyl)diethylamine in 150 ml of chlorobenzene were heated to 100° C. and stirred at this temperature for 3.5 hours. The reaction mixture was diluted with water, the organic phase was separated off, the aqueous phase was extracted with methyl tert-butyl ether, the organic phase was washed with water, and the organic phase and the extract from the aqueous phase were combined. After drying it over sodium sulphate, the solvent was removed in vacuo. A yield of 85% of theory of D-threo-(–)-2-phenyl-4-(fluoromethyl)-5-(4-methylsulphonyl)-phenyl-2-oxazoline was obtained (determined by HPLC).

Example 2

10 g of D-threo-(–)-2-phenyl-4-(4-(methylsulphonyl)phenyl)-2-oxazole-5-methanol and 15 g of N-(1,1,2,3,3,3-hexafluoropropyl)diethylamine in 150 ml of tetramethylene sulphone were heated at 100° C. for 3 hours. The reaction mixture was worked up as described in Example 1. 10 g of the same compound as in Example 1 were obtained, which corresponds to a yield of 82% of theory.

Example 3

10 g of D-threo-(–)-2-phenyl-4-(4-(methylsulphonyl)phenyl)-2-oxazole-5-methanol and 15 g of N-(1,1,2,3,3,3-hexafluoropropyl)diethylamine in 120 ml of a dichlorobenzene isomer mixture were heated to 110° C. and stirred at this temperature for 4 hours. Working up of the reaction mixture was carried out as described in Example 1. The same compound as in Example 1 was obtained in a yield of 79% of theory.

What is claimed is:

1. A process for the preparation of a side chain-fluorinated alkyloxazole of the formula

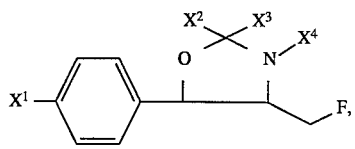

in which $X^1$ represents hydrogen, nitro, $C_1$–$C_6$-alkylthio, $C_1$–$C_6$-alkylsulpho, $C_1$–$C_6$-alkylthio substituted by fluorine, $C_1$–$C_6$-alkylsulphonyl substituted by fluorine $C_1$–$C_6$-alkoxy substituted by fluorine, $X^2$ represents $C_1$–$C_6$-alkyl, $C_1$–$C_6$-halogenoalkyl, $C_5$–$C_7$-cycloalkyl, $C_2$–$C_6$-alkenyl, $C_2$–$C_6$-alkinyl, $C_1$–$C_6$-alkoxy, $C_7$–$C_{14}$-aralkyl, $C_8$–$C_{15}$-aralkenyl, $C_6$–$C_{12}$-aryl or a heterocyclic radical having 4 to 11 C atoms and 1 to 3 oxygen, sulphur and/or nitrogen atoms, $X^3$ represents hydrogen or one of the radicals indicated in the case of $X^2$ or $X^2$ and $X^3$ together represent an oxygen atom and $X^4$ represents hydrogen or $X^3$ and $X^4$ together represent a covalent bond, in which the appropriate hydroxyalkyloxazole of the formula (II)

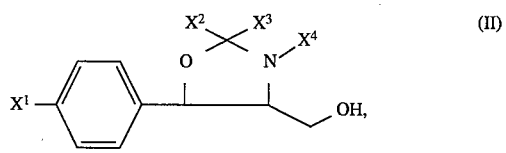

in which the radicals $X^1$ to $X^4$ have the meaning indicated in formula (I), is reacted with an α,α-difluoroalkylamine of the formula (III)

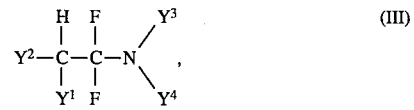

in which $Y^1$ represents fluorine or chlorine, $Y^2$ represents fluorine, chlorine or trifluoromethyl and $Y^3$ and $Y^4$ independently of one another represent $C_1$–$C_6$-alkyl or $Y^3$ and $Y^4$ together represent a saturated or unsaturated hydrocarbon chain having 4 to 5 C atoms, in which process the reaction is carried out at pressures of 0.1 bar to atmospheric pressure and in the presence of an inert solvent boiling at above 100° C. (at normal pressure).

2. The prorocess of claim 1, in which in the formulae (I) and (II), $X^1$ represents $C_1$–$C_3$-alkylsulphonyl, $X^2$ represents phenyl or naphthyl and $X^3$ and $X^4$ together represent a covalent bond.

3. The process of claim 1, in which relative to 1 mol of a compound of the formula (II), 0.8 to 5 equivalents of a compound of the formula (III) are employed.

4. The process of claim 1, in which the solvent employed is tetramethylene sulphone, chlorobenzene, a dichlorobenzene or a trichlorobenzene.

5. The process of claim 1, which is carried out at 70° to 150° C.

6. Side chain-fluorinated alkyloxazoles of the formula

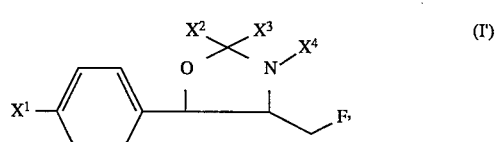

in which $X^1$ represents $C_1$–$C_6$-alkylthio substituted by fluorine, $C_1$–$C_6$-alkylsulphonyl substituted by fluorine or $C_1$–$C_6$-alkoxy substituted by fluorine, $X^2$ represents $C_1$–$C_6$-alkyl, $C_1$–$C_6$-halogenoalkyl, $C_5$–$C_7$-cycloalkyl, $C_2$–$C_6$-alkenyl, $C_2$–$C_6$-alkinyl, $C_1$–$C_6$-alkoxy, $C_7$–$C_{14}$-aralkyl, $C_8$–$C_{15}$-aralkenyl, $C_6$–$C_{12}$-aryl or a heterocyclic radical having 4 to 11 C. atoms and 1 to 3 oxygen, sulphur and/or nitrogen atoms, $X^3$ represents hydrogen or one of the radicals indicated in the case of $X^2$ or $X^2$ and $X^3$ together represent an oxygen atom and $X^4$ represents hydrogen or $X^3$ and $X^4$ together represent a covalent bond.

7. Fluorinated alkyloxazoles of claim 6, in which in formula (I') the radical $X^1$ is monofluorinated or polyfluorinated or perfluorinated.

8. Fluorinated alkyloxazoles of claim 6, in which in formula (I'), $X^1$ represents methyl or ethylthio, methyl or ethylsulphonyl or methoxy or ethoxy which are substituted by 1 to 3 F atoms in each case, $X^2$ represents phenyl or naphthyl and $X^3$ and $X^4$ together represent a covalent bond.

* * * * *

UNITED STATES PATENT AND TRADEMARK OFFICE
CERTIFICATE OF CORRECTION

PATENT NO. : 5,621,111
DATED : April 15, 1997
INVENTOR(S) : Lui, et al.

It is certified that error appears in the above-indentified patent and that said Letters Patent is hereby corrected as shown below:

Col. 4, line 30    Delete " prorocess " and substitute -- process --

Signed and Sealed this

Eighth Day of July, 1997

*Attest:*

BRUCE LEHMAN

*Attesting Officer*    *Commissioner of Patents and Trademarks*